United States Patent [19]

Lim et al.

[11] Patent Number: 5,120,648
[45] Date of Patent: Jun. 9, 1992

[54] CHEMICAL ANALYZER USING RF RADIATION ATTENUATION MEASUREMENTS

[75] Inventors: Franklin Lim; William H. Bingham, both of Richmond; Richard D. Moss, Chester; Lloyd T. Hall, III, Richmond, all of Va.

[73] Assignee: Lim Technology Laboratories, Inc., Richmond, Va.

[21] Appl. No.: 199,229

[22] Filed: May 26, 1988

[51] Int. Cl.$^5$ .................. C12M 1/40; C12M 1/34; C12N 13/00; G01N 00/00

[52] U.S. Cl. .................. 435/173; 435/288; 435/291; 436/34; 436/147; 436/148; 422/68.1; 422/108; 73/61.41

[58] Field of Search .................. 435/291, 288, 4, 173; 324/58.5 A, 61 P, 442, 446, 447, 448, 449, 616, 637, 639; 342/22; 436/34, 183, 147, 148, 149, 806; 422/68, 75, 83, 108; 73/53, 61.1 R

[56] References Cited

U.S. PATENT DOCUMENTS

| | | | |
|---|---|---|---|
| 3,396,331 | 8/1968 | Sperry, III | 324/30 |
| 3,404,335 | 10/1968 | Kidder | 324/30 |
| 3,404,336 | 10/1968 | Rosenthal | 324/30 |
| 3,417,329 | 12/1968 | Landis et al. | 324/62 |
| 3,421,982 | 1/1969 | Schultz et al. | 195/103.5 |
| 3,482,161 | 12/1969 | Poulter | 324/58.5 A |
| 3,483,860 | 12/1969 | Namerow | 324/58.5 A |
| 3,765,841 | 10/1973 | Paulson et al. | 23/230 |
| 3,811,087 | 5/1974 | Schmelzer | 324/58.5 A |
| 3,981,082 | 9/1976 | Massey | 324/58.5 A X |
| 4,713,347 | 12/1987 | Mitchell et al. | 436/501 |
| 4,745,353 | 5/1988 | Stewart et al. | 324/585.5 A |
| 4,765,179 | 8/1988 | Fuller et al. | 73/53 |

OTHER PUBLICATIONS

W. Scott et al., "A New Radiofrequency Titrimeter", *THE ANALYST*, vol. 95, No. 1127, Feb. 1970.

E. Pungor et al., "The Dielectric Constant and Oscillometric Measurement", *MIKROCHIM. ACTA*, 1966/4–5.

E. Pungor et al., "The Oscillometric Measurement of Electric Conductivity Based Flow-Through Cell", *ELECTROCHEMICAL DETECTION IN FLOW ANALYSIS*, 1982.

R. Megargle et al., "A Cell for Dielectrometric Titrations", *ANALYTICAL CHEMISTRY*, vol. 44, No. 6, May 1972.

R. Megargle et al, "Dielectrometric Titrations: Nonquantitative Reactions", *ANALYTICAL CHEMISTRY*, vol. 42, No. 11, Sep. 1970.

Primary Examiner—Robert J. Warden
Assistant Examiner—T. A. Trembley
Attorney, Agent, or Firm—Burns, Doane, Swecker & Mathis

[57] ABSTRACT

A chemical analyzer in which the measurement of the change in attenuation of RF radiation propagated through a sample is used as the basis for calculating the change in concentration of a given chemical in the sample. Also disclosed are various probe and system designs which facilitate the use of RF attenuation as a basis for measurement of certain chemical characteristics of a sample.

43 Claims, 13 Drawing Sheets

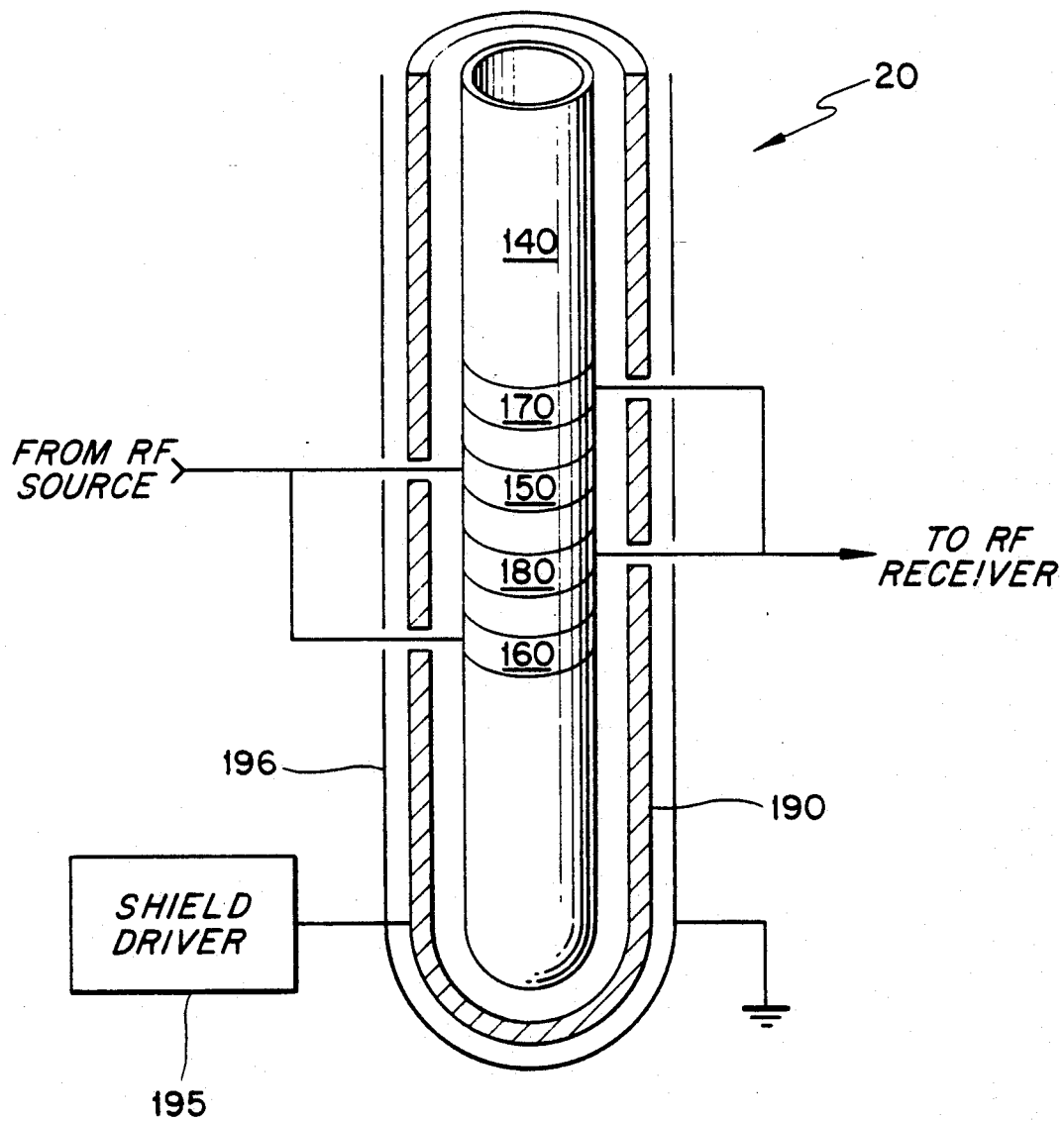

CHEMICAL ANALYZER USING RF RADIATION ATTENUATION MEASUREMENTS

BACKGROUND OF THE INVENTION

1. Field of the Invention

This invention relates to the field of chemical analysis and, more specifically, to the interaction of electromagnetic radiation with a sample to determine certain intrinsic characteristics such as the rate at which a chemical reaction may be progressing, and by extension the concentration of one or more specific components in the sample.

This invention pertains even more particularly to a chemical analyzer which employs a contactless methodology, based on the transmission of electromagnetic radiation in the radio frequency ("RF") range along a known path through a volume element of a sample.

This invention also relates to various probe and system designs which facilitate the use of RF radiation attenuation as the basis for the measurement of certain chemical characteristics of a sample.

2. Background Art

One ordinarily skilled in chemical analysis is generally familiar with a variety of apparatus which measure changes in the way a sample interacts with an electromagnetic field to obtain a measure of the concentration or change in concentration of components in the sample.

One example of such a device is the conductivity meter. As the name implies, these devices measure the electrical conductivity of the sample. Most of these devices have electrode probes which must be placed in contact with the sample. This is known to create several disadvantages, including sample contamination, probe contamination, and probe degradation. Several other classes of devices avoid the necessity of placing a probe in contact with the sample. These include spectrophotometers and high frequency titrators.

Spectrophotometers measure changes in a light signal as it is propagated through a sample. This makes them suitable for chemical analysis of compounds which interact with radiation of the infrared, visible, and ultraviolet frequencies. Compounds which do not interact with these frequency ranges, however, are not susceptible to measurement by such devices.

High frequency titrators represent the first attempts at measuring changes in sample interactions with RF fields. They measure resistance, capacitance, or inductance of a tuned circuit incorporating the sample. As a result they are, as a class, susceptible to changes in complex impedances and exhibit nonlinear response and calibration problems.

SUMMARY OF THE INVENTION

There thus exists a need for a device which measures, directly or indirectly, the change of concentration of one or more species in a sample without contaminating the sample or fouling the sampling sensors. The present invention resides in a system which monitors the aforementioned change in concentration which may be brought about by chemical reaction, light, heat, pressure or other means. This rate information is then converted into concentration information via internally stored rate to concentration translation data.

Rate data is acquired by monitoring alterations in the RF attenuation of the sample during the change in concentration. As with high-frequency titrators the present invention eliminates the need for sensors which are in contact with the sample. Thus, problems of sample contamination, instrument contamination, and probe degradation are avoided. However, as a result of its novel design, the present invention possesses much greater sensitivity and wider concentration response than previous devices.

Additional merits of a chemical analyzer according to the present invention are that it lends itself to automation, can be made analyte specific, can be operated in either a batch or continuous flow manner, and can be easily employed to monitor species contained in a sterile environment. Furthermore, the chemical analyzer according to the present invention can perform analysis on samples of microliter volume.

BRIEF DESCRIPTION OF THE DRAWINGS

These and other features of the advantages of the invention can be more fully understood from the following written description read in conjunction with the drawings, in which:

FIG. 2 is a partially cut-away view of a cell and antenna electrode arrangement which may be used to particular advantage in a chemical analyzer according to the present invention;

DETAILED DESCRIPTION OF PREFERRED EMBODIMENTS

In the following description, the term "radio-frequency" or "RF" is used to describe signals of electromagnetic radiation having frequencies lying in that portion of the spectrum between about 100 KHz and about 500 MHz. The term "antenna electrode" is intended to refer to any structure used either to transmit or receive RF signals with the goal of monitoring RF attenuation. "Antenna electrode material" refers to any material from which an antenna electrode may be fashioned, including metals, conductive plastics, conductive polymers, and metal films. "Rate to concentration translation" encompasses any process, including selective data retrieval, or algebraic or algorithmic calculation, for translating or converting data concerning a rate of a chemical reaction into data concerning concentration values of various components of that reaction.

Figure 1:
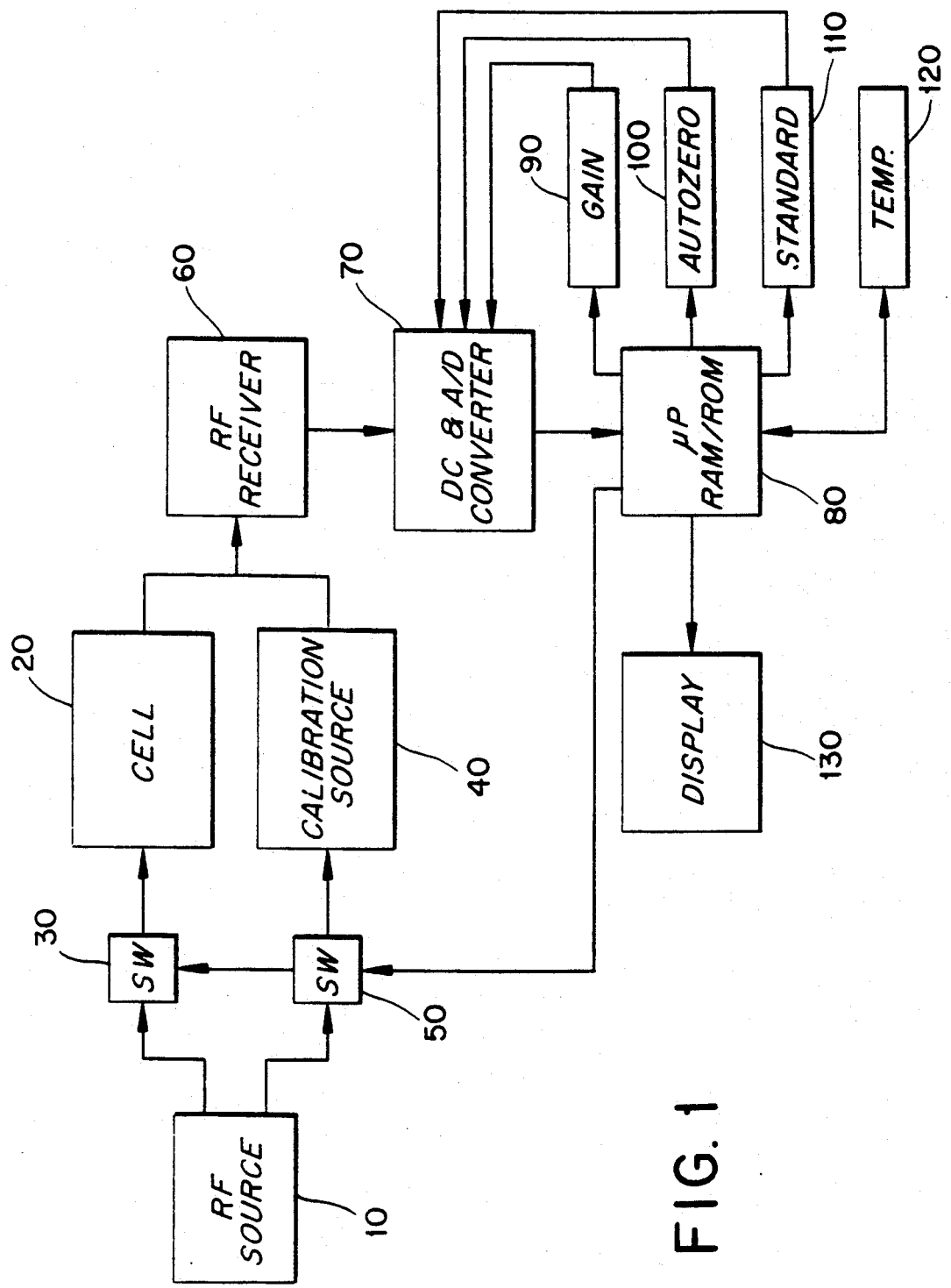
FIG. 1 is a functional block diagram of one embodiment of a chemical analyzer according to the present invention.

With these terms in mind, and with reference first to FIG. 1, a chemical analyzer according to the present invention comprises a source 10 of an amplitude-stabilized signal having a frequency in the radio frequency (RF) range of the electromagnetic spectrum, i.e., anywhere from about 100 KHz to about 500 MHz. Its amplitude will generally be between 1 and 100 volts, plus or minus, depending on the intended application of the chemical analyzer. The frequency may either be fixed or variable, again depending on the intended application.

The RF signal from the RF source 10 is applied to a cell 20. The cell 20 is designed to retain a volume element of the sample under consideration. The words "cell" and "retain" as used in this specification and appended claims are intended to encompass both an arrangement in which the volume element is contained in the cell, as well as that in which the volume element is adjacent to, surrounds, or is in any other fashion maintained in proximity to the antenna electrodes. Proximity here is defined in terms of geometry. Actual distances vary with materials and environment.

The cell 20 is provided with some form of antenna electrode structure, to be described more fully below. The antenna electrodes are arranged so that one transmits an RF signal to the other through the sample volume element. Stated another way, the antenna electrodes direct the RF signal, or "first" signal, along a known path passing through a volume element of the sample. The volume element attenuates the first signal to a degree indicative of the chemical concentration of the sample. The opposing antenna electrode(s) thus receive an attenuated RF signal, or "second signal".

It will, in general, be useful to provide some means for obtaining a baseline or calibration measurement. One such means is shown in FIG. 1. A pair of switch units 30 and 50 are used to couple selectively the signal either through the sample or along a path of known attenuation. For example, when the RF signal from the RF source 10 is applied to the cell through first switch unit 30 when closed, no RF signal will be applied to the calibration source 40. Alternatively, if no RF signal is applied via the first switch unit 30, the RF signal is applied via second switch unit 50 to a calibration source 40 which attenuates the RF signal in a known fashion. This calibration source 40 may be any device having a stable and known attenuation such as an RC network or a sealed standard solution. The calibration source 40 permits the measurement circuitry, described below, to compensate for changes in measured values resulting from component drift and line voltage fluctuations.

Once the RF signal has traveled a path through either a volume element of the sample or the calibration source 40 and has become an attenuated RF signal or second signal, it is detected by measurement means which include an RF receiver 60. The RF receiver 60 produces an analog signal the level of which indicates the degree of attenuation of the RF signal.

The measurement means also includes signal conditioning and analog-to-digital conversion (AD) circuitry 70. The converter 70 operates in a known fashion to produce a digital representation of the voltage level of the conditioned analog signal originating from the RF receiver 60. The converter 70 may also perform additional signal conditioning including variable or differential amplification and autozeroing.

The digital signal from the converter 70 is applied to a calculating means 80. In a preferred embodiment of the invention, the calculating means 80 is a suitably programmed microprocessor with associated random access memory (RAM) and read only memory (ROM). The microprocessor may be programmed to perform any one of a number of types of data analysis, depending on the types of information ultimately desired. For example, the calculating means 80 may monitor the system for deviation above or below certain set points and provide a "yes or no" type response when such deviations occur.

Alternatively, the calculating means 80 may make a determination of the initial rate of the reaction and use this information to extrapolate reactant's initial concentration. Initial rates of reaction can be correlated with a high degree of accuracy to reactant concentration if the kinetics of the reaction are known.

As shown in FIG. 1, the calculating means 80 can employ feedback to control the gain of the converter 70 through a gain block 90, the DC level or "autozeroing" of the converter 70 through an autozero unit 100, or the calibration of the converter 70 through a standardization unit 110. Suitable feedback algorithms for use in these applications will be apparent to one of ordinary skill in the art. The calculating means 80 can read lookup tables, mathematical functions or heuristic algorithms from an associated ROM which may be used to convert the binary indication of voltage level received from the converter 70 to a concentration value.

As the correlation between voltage level and concentration value is a function of temperature, the system may also include a temperature sensor 120 to provide the calculating means 80 with an indication of sample temperature.

On the basis of the data supplied to it, the calculating means 80 generates values which are provided to a display 130 to provide a visual indication of concentration values, or of any other parameters which have been selected for display. Display 130 may include a printer, panel display bars, host computer, or a related device.

Design of the cell 20 is an important consideration for obtaining optimal results from an analyzer according to the present invention. The critical factors requiring consideration include thickness and composition of materials interposed between the sample and the antenna electrodes and antenna electrode deployment. This latter consideration subsumes antenna electrode separation and antenna electrode geometry and surface area. The antenna electrodes are ideally arranged to present as little surface area as possible to each other in order to minimize capacitive coupling between antenna electrodes. Focusing techniques may be taken into account in designing and constructing antenna electrodes in order to increase RF power density through the sample.

It will be appreciated that if the specific shape of the cell defines a volume element containing a path for the propagation of an RF signal, from transmitting to receiving antenna electrodes, it is a cell within the contemplation of the present invention.

It will also be noted that all the cell configurations to be described prevent any direct contact between the antenna electrodes and the sample.

In a very simple type of cell usable as the cell 20, plate-shaped antenna electrodes may be positioned opposite each other across the cell, or partially cupping the cell with one antenna electrode above the other. However, these designs are inherently flawed since they exhibit excessive capacitive coupling and poor RF focusing.

A more effective design comprises ring-shaped antenna electrodes encircling the cell and stacked one over the other. Such a design is illustrated in FIG. 2. The cell of FIG. 2 includes a tube-shaped member 140, a transmission antenna electrode array comprising antenna electrode rings 150 and 160, and a receiving antenna electrode array comprising antenna electrode rings 170 and 180. While each array has been shown to include only two rings, more or fewer rings could be used. When more than two antenna electrodes are used the transmitting antenna electrode array and the receiving antenna electrode array are preferably interdigitated so that the rings alternate one from one array and one from the other along the length of tube 140. It has been found that such an interdigitating array enhances RF focussing and yields a cell which is significantly more sensitive to concentration changes than one with single ring pair configurations.

The embodiment of FIG. 2 also includes a shield 190 to prevent outside interference. This shield may be grounded. It is also possible to provide an active shield which is driven by a shield driver 195 as shown. This active shield is disposed inside of a passive, grounded shield 196. The particular type of shielding to be used, or whether to use shielding at all, will depend on the environment of, and the sensitivity required, by a given application.

Figure 3A:
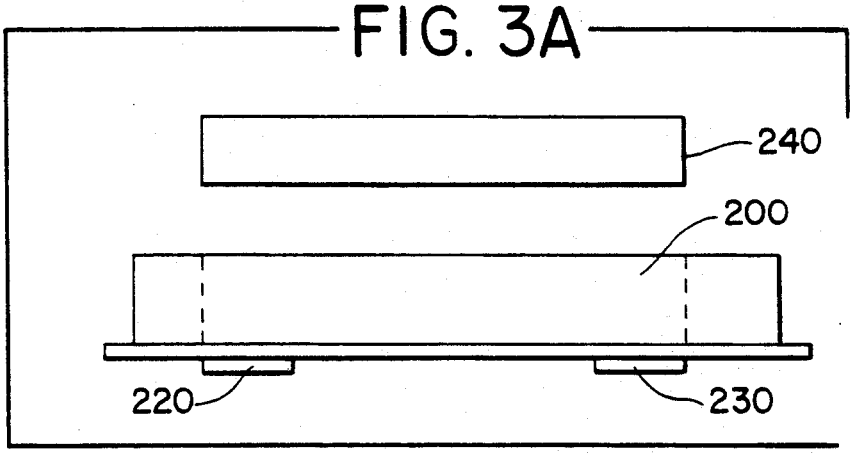
FIGS. 3A and 3B are front and top views of a second embodiment of a cell and antenna electrode arrangement according to a second embodiment of the present invention.
Figure 3B:
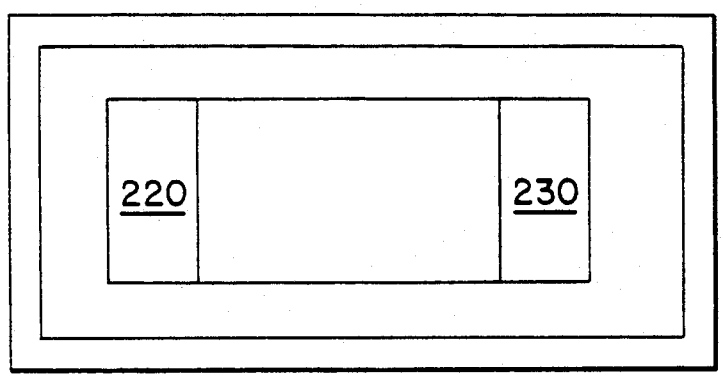

A second type of cell is shown in FIGS. 3A and 3B. It comprises an insulated well 200 affixed to a plate of an insulative material, for example, a sheet of glass. On the other side of and flat to the plate 210 are transmitting antenna electrode 220 and a receiving antenna electrode 230. The antenna electrodes are made, for example, from copper foil but other antenna electrode materials, e.g., metals films, conductive plastics, etc. could be used. In the embodiment of FIGS. 3A and 3B, the well 200 and antenna electrodes 220 and 230 are rectangular. The antenna electrodes 220 and 230 present only their edges to each other thereby decreasing capacitive coupling.

A sponge 240 may be placed in the well 200 which will absorb the liquid sample. This sponge provides a predefined sample path and may be impregnated with any enzymes or buffers required for the reaction. It also helps to prevent sample spillage.

Figure 4:
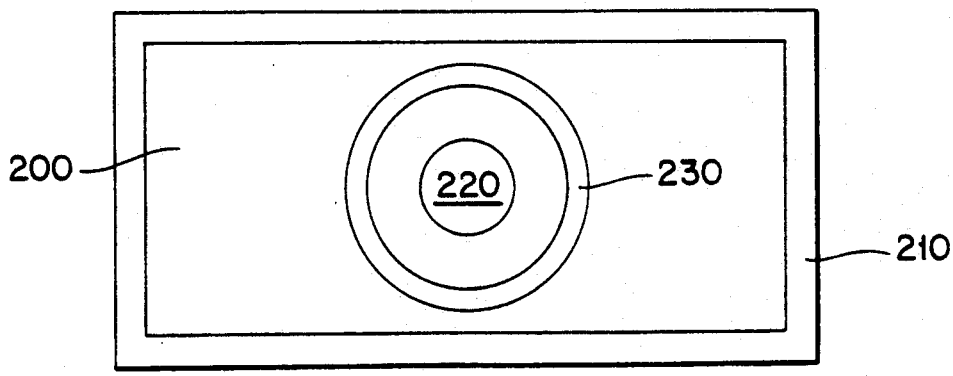
FIG. 4 is a top view of a modification of the arrangement of FIGS. 3A and 3B to yield a third embodiment.

A third type of cell includes a generally circular antenna electrode and well arrangement is shown in FIG. 4. Antenna electrode 220 is shaped as a central plate or disk and antenna electrode 230 as a surrounding ring. It has been found that this arrangement provides more sensitivity than the rectangular arrangement. On the other hand, the rectangular arrangement requires less volume to achieve full sensitivity. Other well configurations are possible and may be preferred in some applications.

Figure 5A:
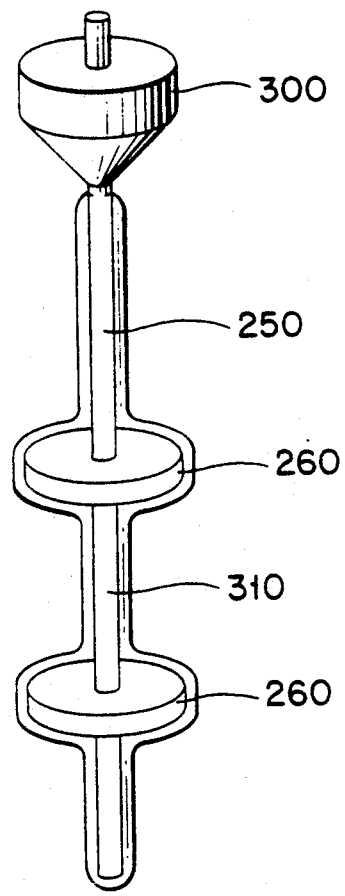
FIGS. 5A and 5B are front views of a fourth embodiment of a cell and antenna electrode assembly according to a third embodiment of the present invention.
Figure 5B:
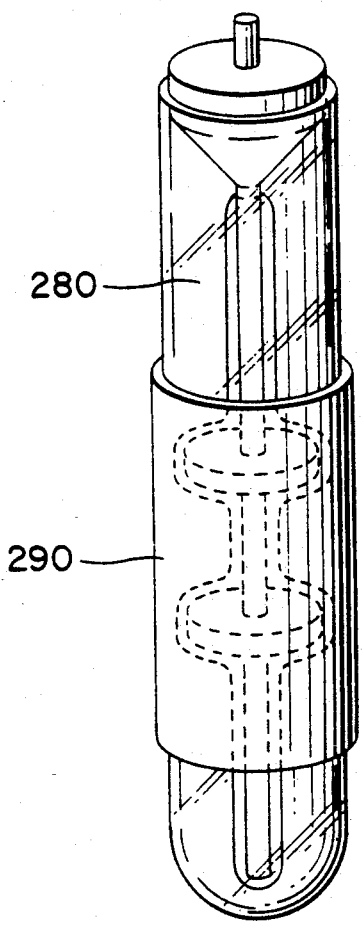

FIGS. 5A and 5B show a fourth embodiment which will be referred to as a dip-type arrangement. FIG. 5A shows a transmitting antenna electrode. It has a rodlike support 250 with either disc-shaped or corona-shaped radiating surfaces 260 attached perpendicular to the rod 250. The entire transmitting antenna electrode is coated with an insulative material. FIG. 5B shows the receiving antenna electrode can be shaped like a conventional test tube 280 with a wrap of copper foil 290 or other antenna electrode material about it. The transmitting antenna electrode is inserted into tube 280 to form the complete cell. The sample is contained within tube 280. The benefits of this design are that the tube 280 may be made disposable. It may further have reactants and/or buffer solutions in it. The rodlike member 250 may be provided at its upper end with a stopper member 300 for sealing the tube 280.

Figure 6A:
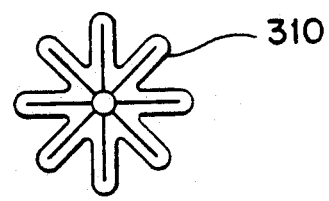
FIGS. 6A and 6B are top views of two embodiments of part 260 from FIG. 5A.
Figure 6B:
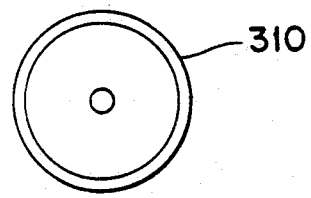

FIGS. 6A and 6B show preferred configurations for the radiating surfaces 260. FIG. 6A shows a corona-type configuration while FIG. 6B shows a disk-type configuration. Other configurations are possible. The antenna electrode surfaces may be provided with a coating 310 such as glass, plastic or wax to provide isolation from the sample.

Figure 7:
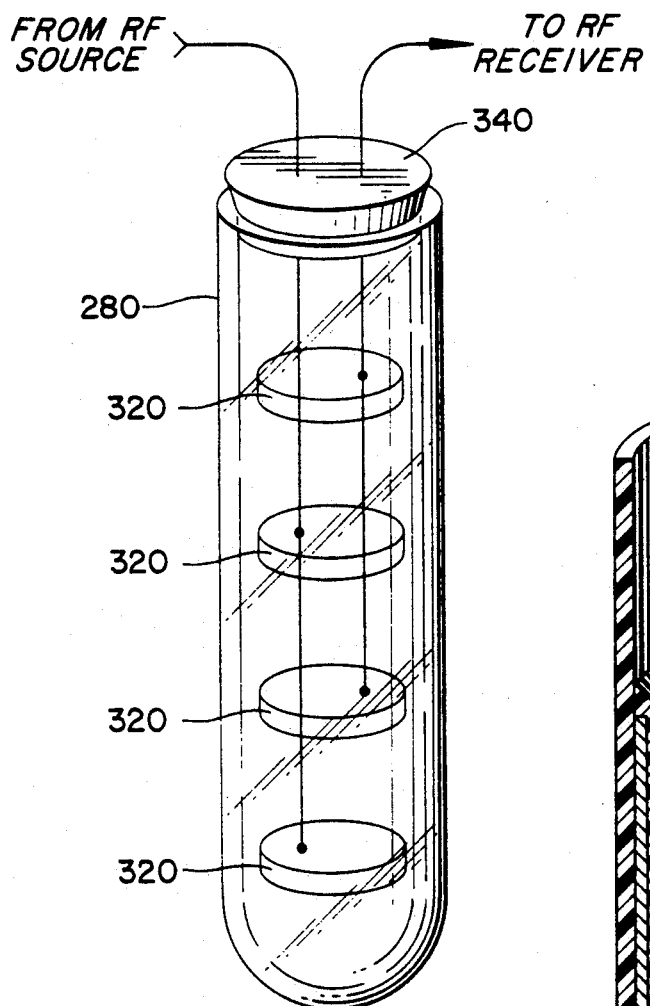
FIG. 7 is a front view of a fifth embodiment according to the present invention.

As opposed to the embodiments previously described in which the volume element of the sample is confined within the cell, a fifth arrangement shown in FIG. 7 is useful in applications where it is more convenient to put the sensor assembly into the sample. An example would be where there is a very large volume of sample to be monitored, as with batch fermentors. This design is an eversion of the cells previously described. Thus, rather than placing an electrode antenna on the outside of the cell and the sample on the inside, antenna electrodes 320 are disposed inside a tube 280 which is then sealed with a plug 340. A cell such as that shown in FIG. 7 is thus submersible, the sample being around rather than inside the tube.

Figure 8:
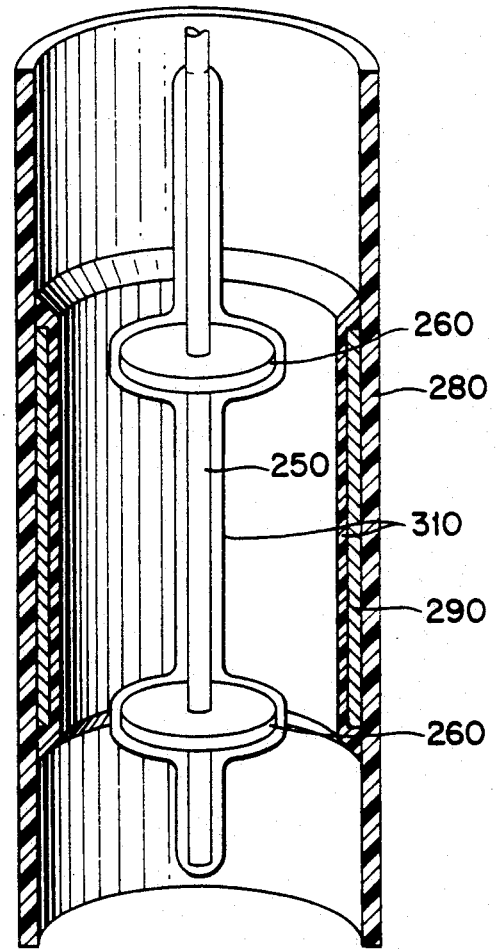
FIG. 8 is a partially cut-away front view of a sixth embodiment of a cell and electrode assembly according to the present invention.

A sixth sensor embodiment is shown in FIG. 8. This embodiment is also a submersible type and can be conceived of as a modification of those shown in FIGS. 5A and 5B. The tube 280 in the embodiment of FIG. 8 is open at both ends. The antenna electrode 290 is disposed on the inside surface of the tube 280. The coating 310 isolates the antenna electrode 290 from the interior of the tube 280, which in the arrangement shown will contain sample. Rodlike member 250 with coated radiating surfaces 260 is disposed inside the tube 280. This yields the improvement of a cell which is open to the greater environment while restricting the RF path to a defined configuration.

Figure 8A:
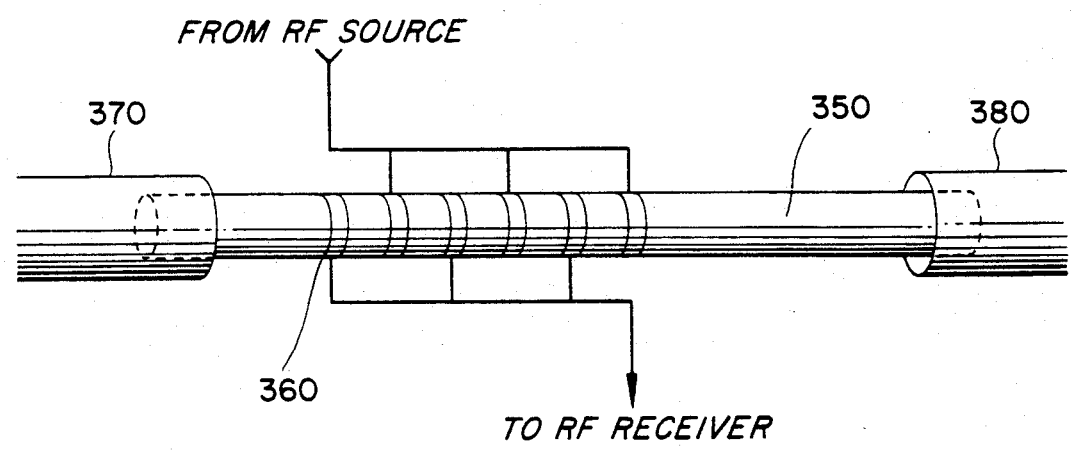
FIG. 8A is a front view of a seventh embodiment according to the present invention.

A cell embodiment similar to that of FIG. 2 is shown in FIG. 8A. This cell is of a flow-through type which would be useful in a continuous flow or automated testing environment. It includes a tube 350 of insulative material with a ring-type antenna electrode array 360 arranged similarly to that of FIG. 2. One end of the tube is connected to an inlet tube 370 and the other end is connected to an outlet tube 380 so that fluid may flow through the cell.

An alternative embodiment for cell construction and particularly antenna electrode creation can be obtained by either sputtering, electrochemically or chemically depositing metal onto the cell, rather than by physically positioning discrete metal antenna electrodes about the cell. This has advantages for both precision and for cost effectiveness in large scale production. This type of antenna electrode system lends itself to several replaceable mounting techniques. For example, spring metal clips could be used to make contacts with metal rings which are deposited on either surface of a test cell. It is also possible to use carbon- or metal-impregnated plastics or other conductive polymers as antenna electrodes. Impregnated plastics would be washable, deformable, and shapeable. The capability of making exotic shapes, of mass producing the antenna electrodes, and of achieving overall cost effectiveness would all accrue from using such electrodes. This will significantly ease the design of systems requiring many cell changes and will facilitate sterilization and clean-up procedures. For example, simple deformable clamps made of such plastics and acting as antenna electrodes could be designed to hold almost any shaped cell making contact as precise and reproducible as desired.

It should also be noted that it may be desired in studying a certain sample to vary antenna electrode separation as an independent variable. Such variation may be accomplished by either physical or electronic means. Cell design may be influenced by a decision to utilize this method of altering the RF path.

As set forth above, one embodiment of the present invention could include a single set of antenna electrodes in configurations as set forth above. It may also include multiple sets of antenna electrodes on a single cell to greatly increase the sensitivity of the cell.

It is important to note that the theory of operation of a chemical analyzer according to the present invention is different from any hitherto known or used. Previous attempts to use high frequency, contactless measurement methodologies have employed measurements of capacitive, resistive or inductive effects. The present invention, on the other hand, contemplates measurement of dielectric loss as manifested by RF attenuation, that is, the electromagnetic energy which a dielectric absorbs and converts to other forms of energy when a periodic electromagnetic force (EMF) is propagated through it. This loss is a function of the dielectric absorption of the sample and of frequency. The dielectric absorption of the sample will depend on the concentrations of the various chemical components of the sample.

The chemical analyzer according to the present invention can be used to study chemical concentration changes in a variety of systems. It may be used as a detector in biological systems, such as in blood and urine chemistry analysis, in environmental systems such as fermentation systems or cell culture, or in such analytical instrumentation applications as, for example, a monitor in a high performance liquid chromatography system. The nature of the invention makes it especially well suited to automated test equipment applications such as automated blood analysis equipment. Further the invention will find a special usefulness in process control or other continuous flow applications.

Figure 9:
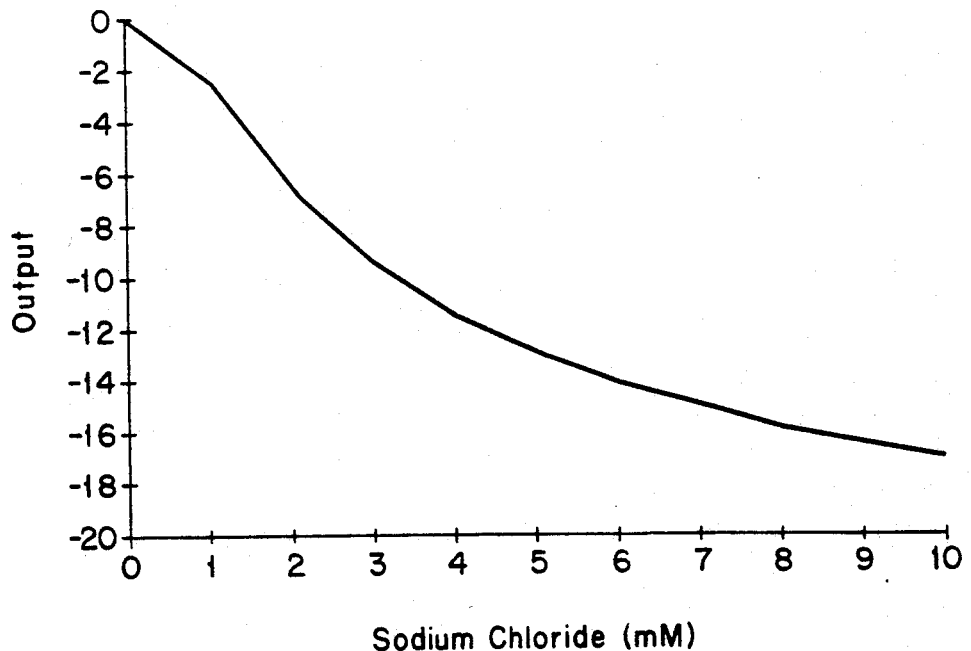
FIG. 9 is a standard curve generated by a chemical analyzer according to the present invention.
Figure 10:
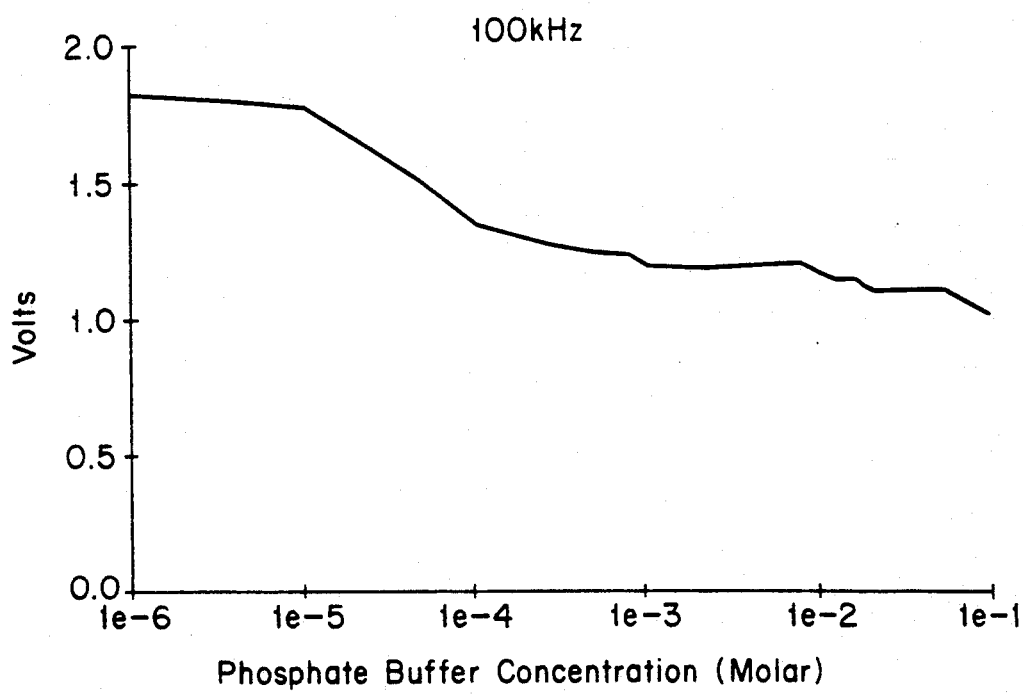
FIGS. 10–15 are graphs which show a response to varying phosphate concentration for several frequencies between 100 KHz and 20 MHz.
Figure 11:
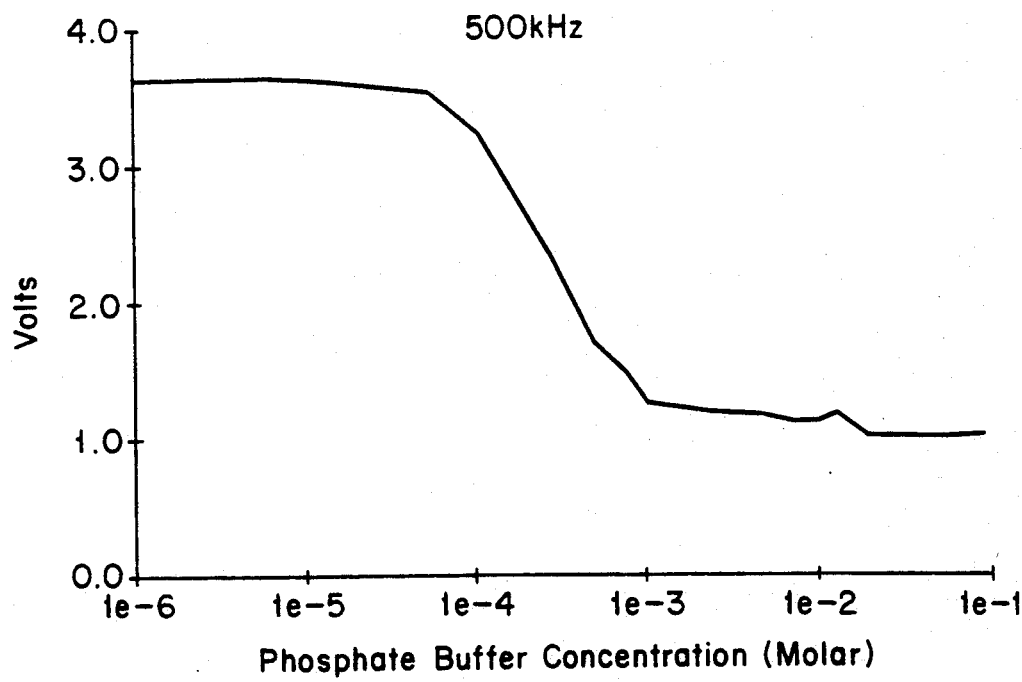
Figure 12:
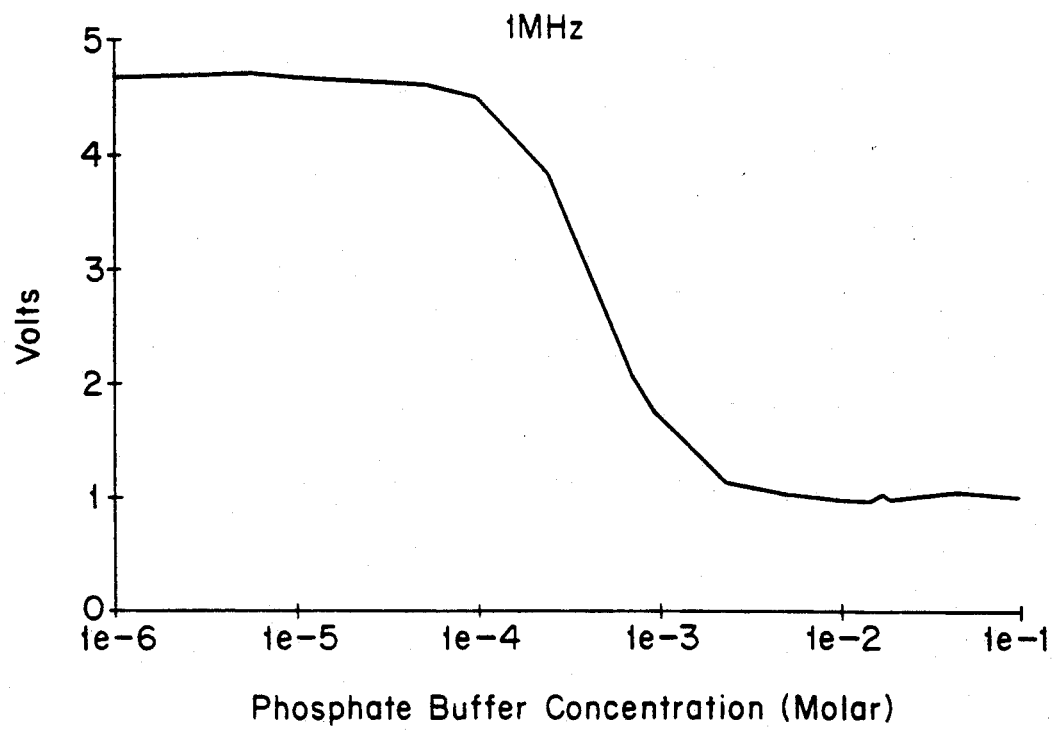
Figure 13:
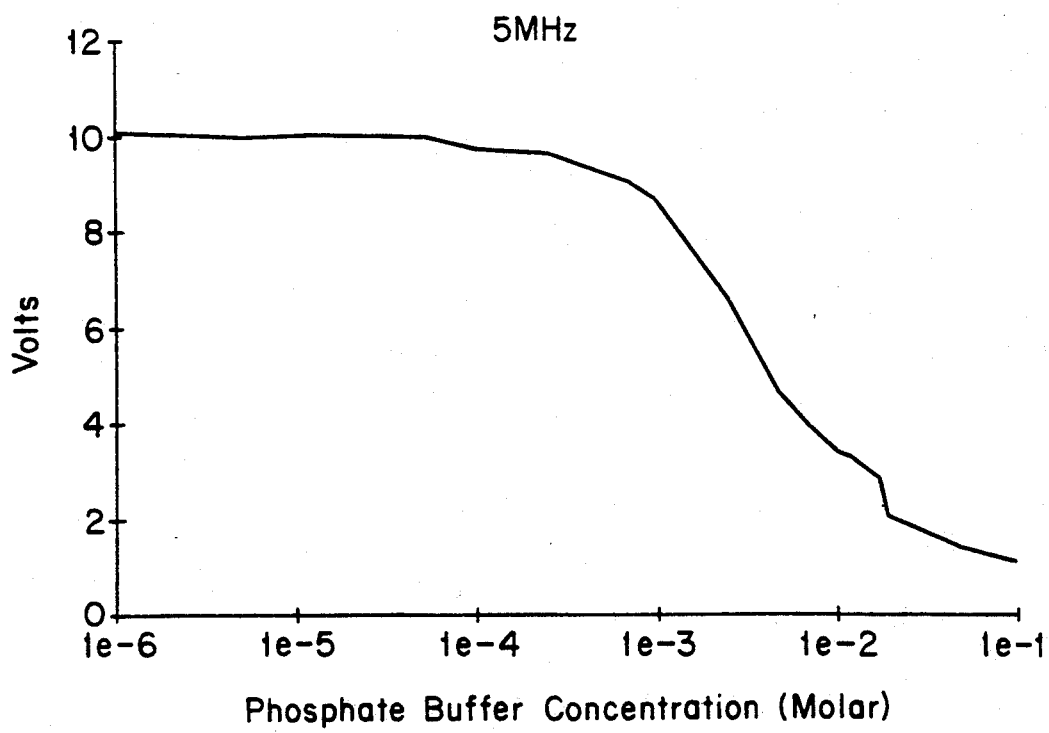
Figure 14:
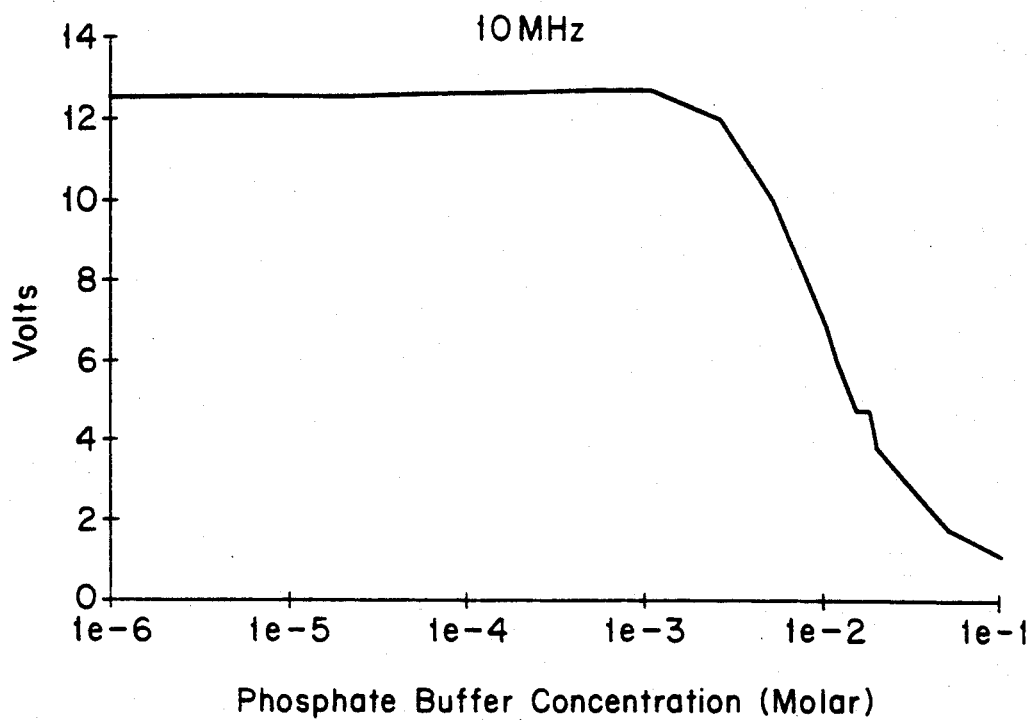
Figure 15:
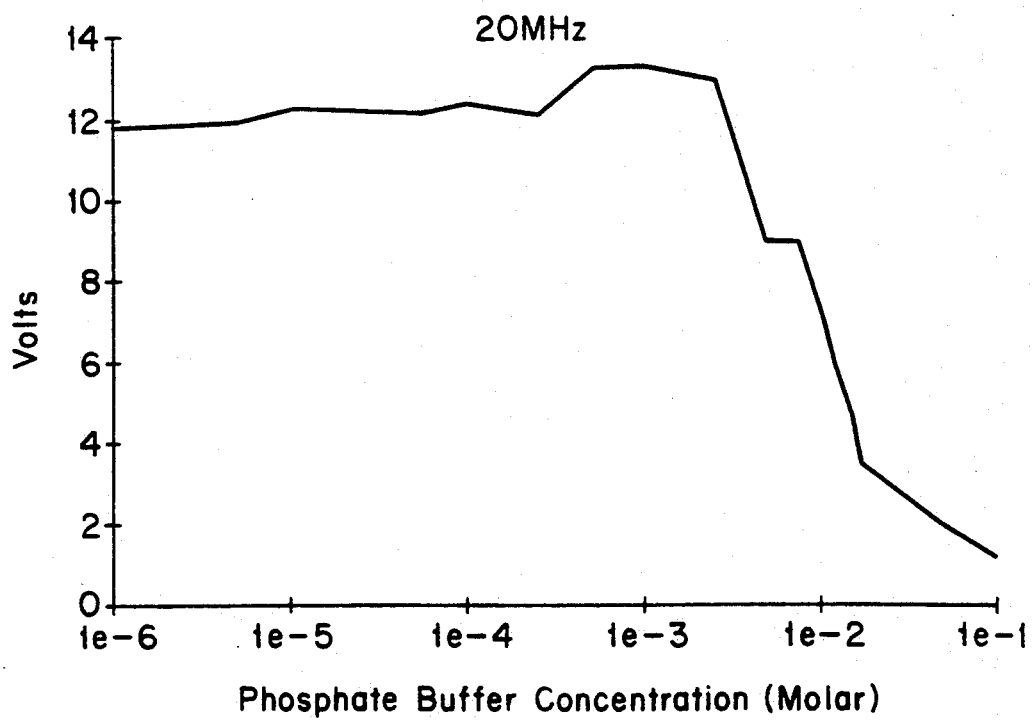

As an example of operation of a chemical analyzer according to the present invention, FIG. 9 shows a standard curve generated by a chemical analyzer operating at 4 MHz. The curve represents the addition of aliquots of known concentrations of NaCl to distilled water. The graph shows that over a certain concentration range, the "active region", the chemical analyzer produces a nearly linear response to concentration change, but that over larger concentration ranges linearity decreases and eventually vanishes. The term "active region" denotes the portion of the curve where attenuation varies nearly linearly as a function of concentration.

Different concentration ranges are more easily probed by different RF frequencies. FIGS. 10–15 are graphs which show the response to phosphate buffer concentration in de-ionized water for several frequencies between 100 KHz and 20 MHz. It can be seen that the active region encompasses higher concentrations with increasing frequency. Thus, frequency sweeping techniques will be an important testing modality for monitoring wide concentration ranges at maximum sensitivity. However, if the concentration range is sufficiently narrow, a single frequency may be selected which spans it, thereby maximizing sensitivity and reducing the cost of the device by eliminating the need for frequency sweeping. These figures show that concentrations from 1 micromolar to 0.1 molar can be brought into the active region. At 20 MHz the active region actually extends to about 1.0 molar and calculations indicate that a device operating at 100 MHz would have a range above 10.0 molar.

Figure 16:
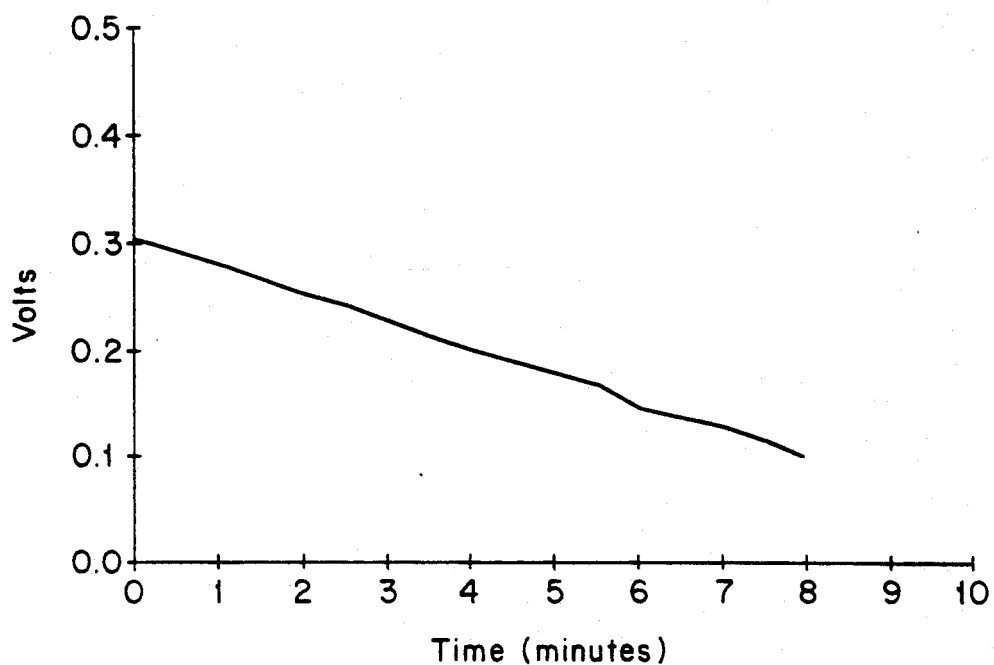
FIGS. 16–17 are graphs showing various types of enzyme reactions tracked by the chemical analyzer.
Figure 17:
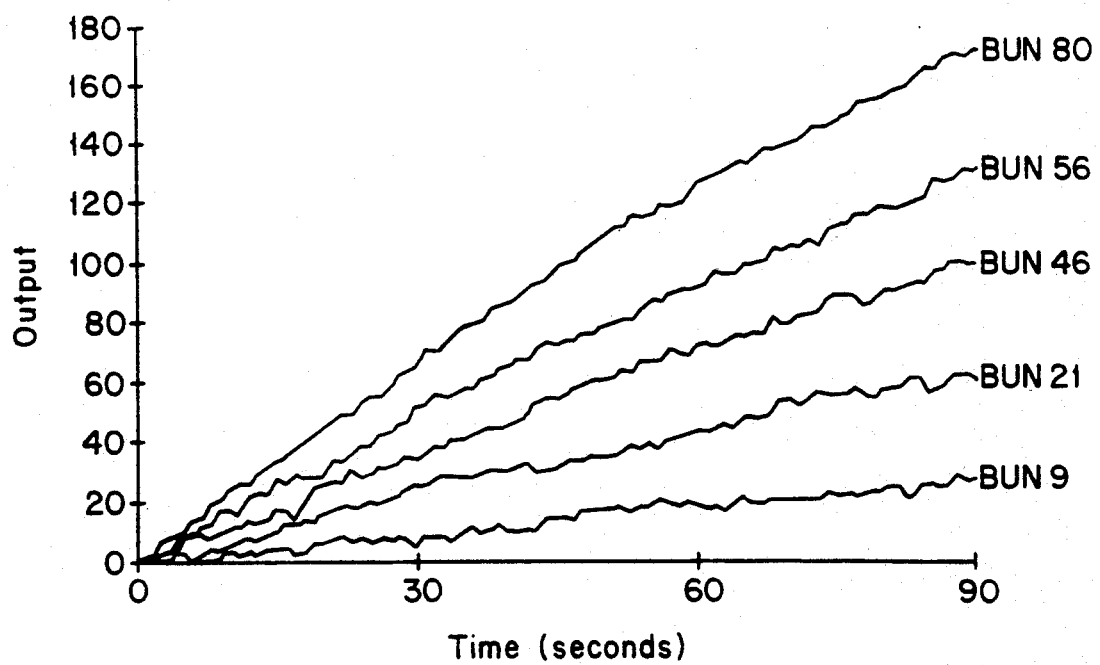

FIGS. 16 and 17 are graphs showing various types of enzyme reactions tracked by the chemical analyzer. The graph of FIG. 16 is of para-nitrophenyl phosphate (PNPP) being degraded by alkaline phosphates (AP), specifically, 1 cc of 66 $\mu$l of 0.625M AMP buffer and 10 mg of PNPP in 20 ml de-ionized water and 5 $\mu$l of 10 mg of 1.1 units/ml AP / 10 ml de-ionized water. The graph of FIG. 17 shows conversions of varying concentrations of urea by urease. In this case the samples are blood serum which have had the BUN, a measure of the urea content, clinically determined. Here it is possible to see the predictable progression of rate of reaction with increasing BUN.

Figure 18:
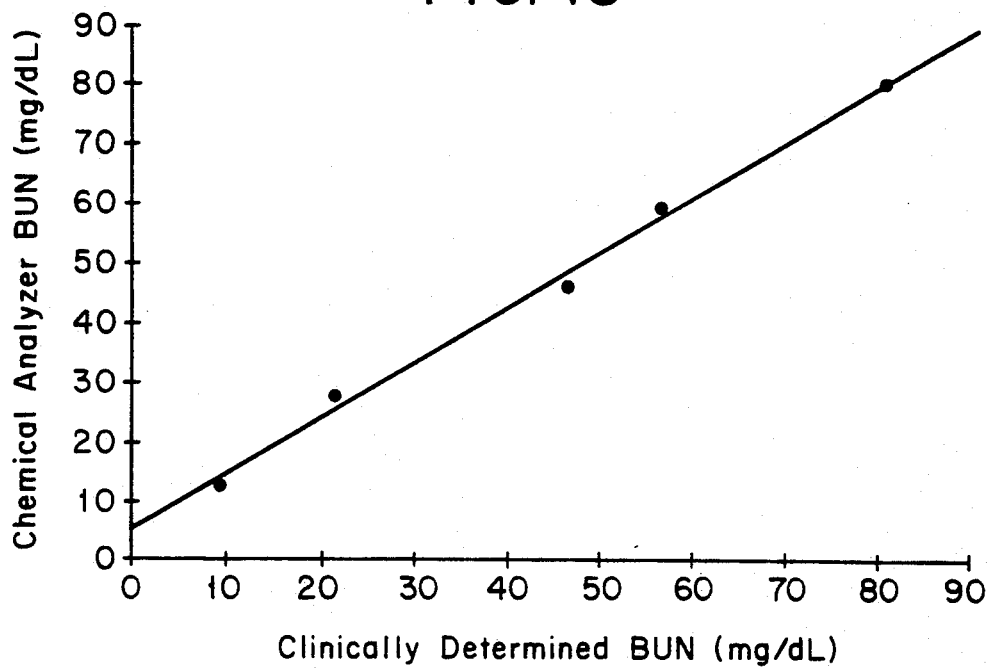
FIG. 18 is a graph showing the degree of correlation between values as determined by an accepted clinical method and values as determined by a chemical analyzer according to the present invention.

From the data on urea shown above, BUN values were calculated and compared to the clinically determined values. The results are shown in FIG. 18. As indicated, the correlation between the two methods was >0.995, well within the margin for error. Calculated BUN values were almost identical whether calculated by reaction rate or by end point determination.

Figure 19:
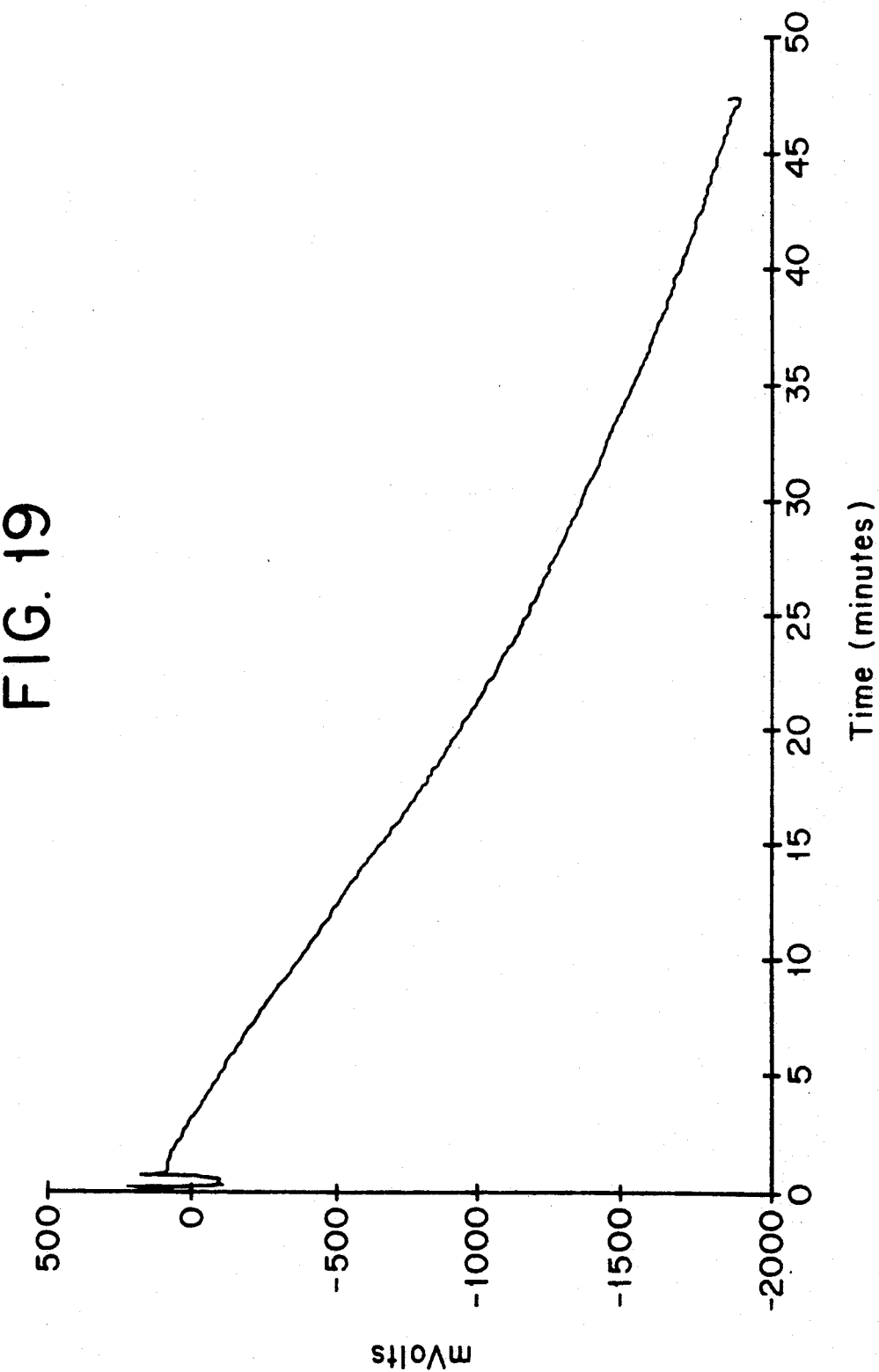
FIG. 19 is a graph showing an enzyme reaction system, employing immobilized enzyme, using the chemical analyzer according to the present invention.

The concept of monitoring enzyme reaction systems with chemical analyzer probes has been discussed. To better control the parameters of the enzyme reaction, the enzyme urease was immobilized onto the walls of a cell. This cell was exposed to a substrate and buffer solution consisting of 10 mM Urea in 2 mM phosphate buffer solution at pH 7.0. The ensuing enzyme mediated reaction was tracked by the chemical analyzer. The results are shown in FIG. 19. This test compared favorably with a similar reaction using a soluble enzyme. The critical factor is maintaining enzyme activity during the immobilization process.

Various types of chemical or biochemical reactions which have been monitored with the chemical analyzer include titrations, rate measurements on soluble and immobilized enzyme systems, and polymerization reactions. It should also be possible to monitor a great many additional types of reactions, including ELISA procedures.

Figure 20:
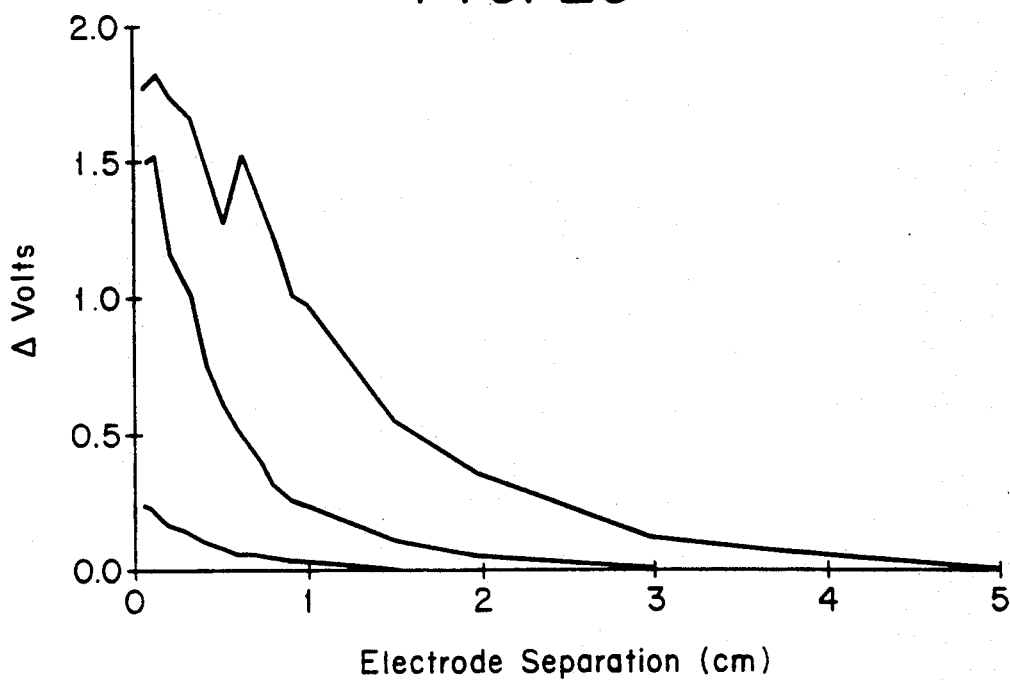
FIGS. 20 and 21 are graphs showing the effects of varying antenna electrode separation on sensitivity.
Figure 21:
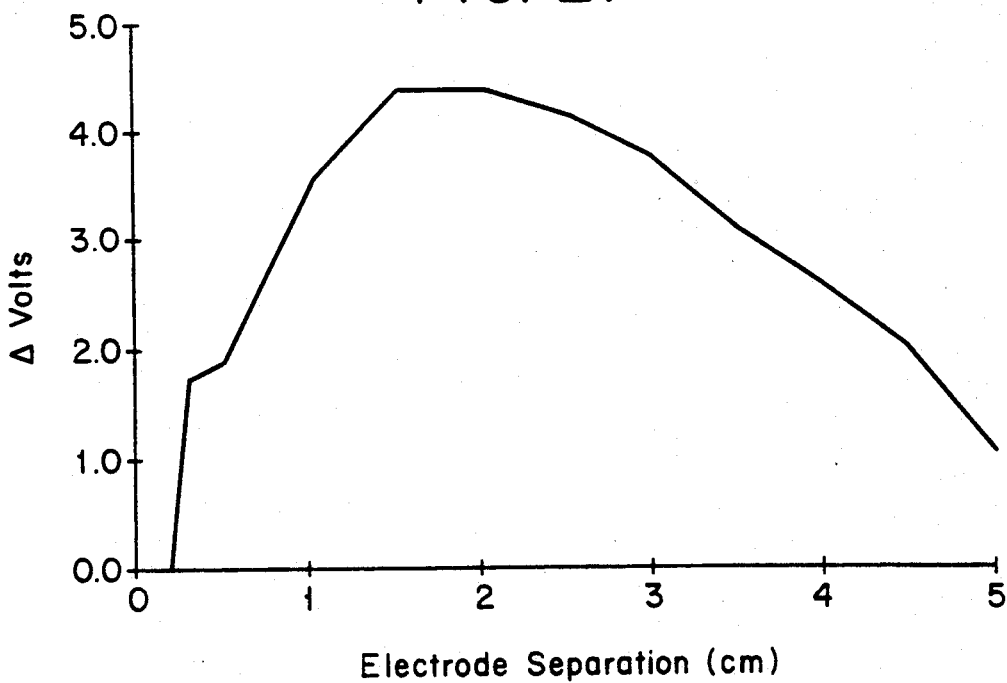

Experiments show that within certain limits the parameters of antenna electrode separation, antenna electrode surface area and the thickness of intervening insulative materials all influence signal attenuation in a linear fashion. More specifically, doubling antenna electrode surface area will roughly double the signal strength. Antenna electrode separation exhibits a more complex relationship which first increases then passes through an inflection point and then may or may not decrease as electrode separation is decreased. Finally, halving the thickness of the intervening insulative material, while using the same material, will also roughly double the signal strength. These relationship will fail if extended too far. An example of the effects of electrode separation and at what limits the relationship breaks down is shown in FIGS. 20 and 21.

Figure 22:
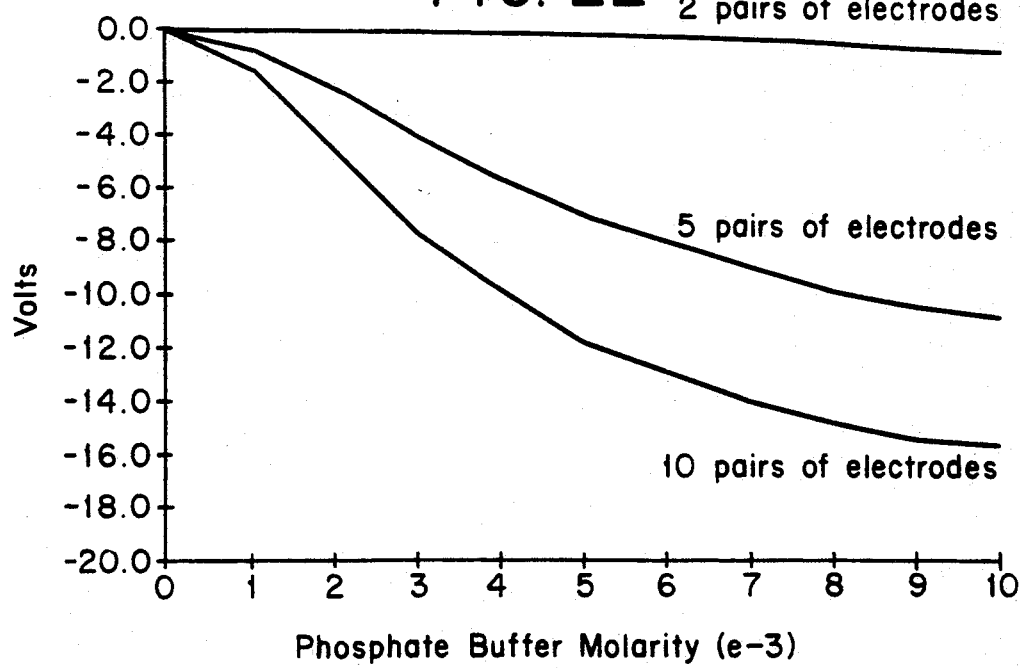
FIG. 22 is a graph showing the effect of RF focussing on chemical analyzer sensitivity.

Experiments show that for certain cell configurations RF focusing techniques which increase the power density through the chosen path also increase sensitivity. One such technique we have discovered is the use of multiple, interdigitated antenna electrode arrays. Cell geometry (here, tube diameter) and electrode number and separation are key factors. FIG. 22 presents a graphical depiction of the effect of electrode pair number on sensitivity.

Cells have been made employing antenna electrodes made from chemically deposited silver and from a conductive plastic. Both types of cells worked satisfactorily.

As will be appreciated from the above, many advantages accrue from the use of RF radiation to probe a sample. Beyond preservation of sample purity and probe integrity, the technique permits great flexibility in probe and cell design. Antenna electrodes may assume a wide range of configurations, or be composed of a wide range of materials. Cells may be of any configuration which, in cooperation with the antenna electrode, define a known path for the propagation of the RF radiation. Moreover, the cells may be provided with immobilized enzymes for analyte specific analysis without the need for frequent enzyme addition.

It will also be appreciated that from the raw RF attenuation data the rate of change of attenuation can be extracted. This in turn yields information concerning rates of change in concentrations of one or more specific analytes. This information can be used to identify crucial points in a reaction, or to provide continuous concentration values. Moreover, when this information is manipulated or compared against stored data, it may serve as a key to inferring many other types of information about the sample.

The present invention has been described above in terms of several specific embodiments. These specific embodiments have been used merely to elucidate the concepts and principles of the invention. They should therefore be regarded as illustrative rather than limiting. Indeed, the invention is not limited to the specific embodiment discussed above, but is instead fully commensurate with the scope of the following claims.

What we claim is:

1. An apparatus for analyzing a sample, comprising:
   means for generating a first signal of radio frequency electromagnetic radiation;
   a transmitting antenna electrode, selectively coupled to said generating means, for directing a first signal along a first path passing through a volume element of a sample to produce a second signal;
   a receiving antenna electrode for receiving said second signal;
   means, coupled to said receiving antenna electrode, for measuring on the basis of said second signal the degree to which said first path attenuates said first signal over a defined interval of time; and
   means, responsive to said measuring means, for correlating the rate of change in attenuation of the first signal to chemical changes occurring in the sample itself.

2. An apparatus as claimed in claim 1, further comprising means, selectively coupled to said generating means, for directing said first signal along a second path of known attenuation, to produce a calibration signal, and wherein said measuring means is arranged to receive said calibration signal and is further for measuring with reference to said calibration signal, said degree to which said first path attenuates said first signal.

3. An apparatus as claimed in claim 1, wherein said means for correlating comprises calculating means, and wherein said measuring means provides data on the rate of change in attenuation of the first signal to said calculating means which determines from stored algorithms a characteristic of the chemical composition of the sample being tested.

4. An apparatus as claimed in claim 3, wherein said calculating means comprises a microprocessor and memory means for retaining a conversion information table containing information correlating the rate of change in attenuation of the first signal with concentration of a chemical in said sample.

5. An apparatus as claimed in claim 1, wherein said correlating means is further for calculating a concentration of a chemical in said sample, based on said measured degree to which said first path attenuates said first signal over said defined interval of time.

6. An apparatus as claimed in claim 5, wherein said correlating means provides a signal indicative of said concentration, and further comprising display means, coupled to said correlating means, for producing a visual indication of said concentration in response to a signal from said correlating means.

7. An apparatus as claimed in claim 5, further comprising a temperature sensing means, arranged to sense the temperature of the sample, for providing an indication of said sensed temperature to said correlating means and wherein said correlating means is further for calculating said concentration additionally with reference to said indication.

8. An apparatus as claimed in claim 1, further comprising cell means for maintaining a volume element of said sample within a few centimeters of at least one of said transmitting and receiving antenna electrodes.

9. An apparatus as claimed in claim 8, wherein said cell means has an outer wall and wherein said transmitting antenna electrode means comprises at least one first antenna electrode disposed coaxially with and on said outer wall, and wherein said receiving means comprises at least one second antenna electrode, disposed on and coaxially with said outer wall, and axially adjacent said at least one first antenna electrode.

10. An apparatus as claimed in claim 8, wherein said cell means comprises a well and said transmitting and receiving antenna electrodes are disposed on an outer surface of the bottom of said well.

11. An apparatus as claimed in claim 10, wherein said well and transmitting and receiving antenna electrodes are rectangular.

12. An apparatus as claimed in claim 10, wherein said well is cylindrical and wherein said pair of transmitting and receiving antenna electrodes is formed as a concentric ring and disk.

13. An apparatus as claimed in claim 8, wherein said cell means comprises a tube-shaped member having an antenna electrode disposed on a longitudinal surface thereof, and a rod-shaped member dimensioned to be disposed within said tube-shaped member and having one or more radiating surfaces arranged thereon.

14. An apparatus as claimed in claim 13, wherein said tube-shaped member is closed at one axial end, and wherein said rod-shaped member is provided with a stopper means for sealing the other axial end of said tube-shaped member.

15. An apparatus as claimed in claim 1, further comprising cell means for physically isolating at least one of said transmitting antenna electrode and said receiving antenna electrode from said sample.

16. An apparatus as claimed in claim 15, wherein said cell means comprises a tube-shaped member sealed at both ends and surrounding said transmitting antenna electrode.

17. An apparatus as claimed in claim 1, further comprising a shield for preventing environmental radio frequency radiation from interfering with transmission of said first signal or with reception of said second signal.

18. An apparatus as claimed in claim 17, wherein said shield is grounded.

19. An apparatus as claimed in claim 17, further comprising means, connected to said shield, for driving said shield to actively prevent environmental radio frequency radiation from interfering with transmission of said first signal or reception of said second signal.

20. An apparatus for analyzing a sample, comprising:
means for generating a first signal of amplitude stabilized radio frequency electromagnetic radiation;
means for propagating said radio frequency electromagnetic radiation along a known path through a sample;
means for inducing a change of concentration of at least one chemical component in said sample for which a change in concentration induces a change in attenuation of said first signal as it is propagated through the sample;
means for repetitively measuring the amplitude of said radio frequency signal over defined, short intervals after it has traversed said known path through said sample; and
means for determining on the basis of the measured amplitude a rate of change of concentration of said at least one chemical component.

21. An apparatus as claimed in claim 20, wherein said generating means is for generating said first signal to have a frequency selected to cause an active region of change in attenuation, wherein attenuation varies nearly linearly as a function of concentration, to occur within an anticipated range of said change in concentration.

22. An apparatus as claimed in claim 20, wherein said generating means is frequency-variable for generating said first signal over a predetermined range of frequencies.

23. An apparatus as claimed in claim 20, wherein said propagating means comprises an absorbent medium for absorbing and immobilizing a quantity of said sample.

24. An apparatus as claimed in claim 20, wherein said propagating means comprises a transmitting antenna electrode and a receiving antenna electrode arranged to couple radio frequency radiation primarily along said known path.

25. An apparatus as claimed in claim 20, wherein said change inducing means comprises an enzyme.

26. An apparatus as claimed in claim 25, further comprising a cell for defining a volume element of said sample, and wherein said enzyme is immobilized on a wall of said cell.

27. An apparatus as claimed in claim 20, wherein said change inducing means comprises means for exposing said sample to light.

28. An apparatus as claimed in claim 20, wherein said change inducing means comprises means for changing pressure of said sample.

29. An apparatus as claimed in claim 20, wherein said determining means comprises a microprocessor and a memory for storing a conversion information table.

30. An apparatus for analyzing a sample, comprising:
a source of RF radiation;
a cell, switchably connected to said RF source and for applying said RF radiation to a volume element of a sample;
a calibration source, switchably connected to said RF source, for producing a known attenuation in said RF radiation when said RF radiation is applied to said calibration source;
receiving means, coupled to said cell and said calibration source, for receiving attenuated RF radiation which has traversed one of said volume element and said calibration source, and for producing analog signals indicative of the magnitude of said attenuated RF radiation;
means, coupled to said receiving means, for converting said analog signals to digital signals;
calculating means, coupled to said converting means, for determining which of said cell and said calibration source is connected to said RF source, for computing the rate of change of attenuation of said RF radiation by said volume element on the basis of digital signals, for determining a change in concentration of at least one component of said volume element on the basis of said computed attenuation; and
means, responsive to said calculating means, for displaying results of said computing.

31. An apparatus as claimed in claim 30, wherein said cell comprises:
means for retaining said sample;
transmitting electrode means for transmitting antenna and focusing said RF radiation through a volume element of said sample; and
receiving antenna electrode means for receiving said RF radiation after said RF radiation has traversed said volume element of said sample.

32. An apparatus as claimed in claim 31, wherein retaining means is substantially cylindrical, wherein said transmitting antenna electrode means comprises a first array of ring-shaped electrodes each surrounding a respective axial portion of said retaining means, and wherein said receiving antenna electrode means comprises a second array of ring-shaped antenna electrodes each surrounding a respective axial portion of said retaining means, said first and second array being interdigitated.

33. An apparatus as claimed in claim 30, further comprising a temperature sensor, arranged to sense temperature of said sample and for generating a temperature signal indicative of the sensed temperature, and wherein said calculating means is coupled to said temperature sensor, and is further for determining said concentration with reference to the sensed sample temperature.

34. An apparatus as claimed in claim 30, further comprising means, coupled to said converting means and responsive to said calculating means for amplification of said attenuated RF radiation which has passed through said volume element of said sample.

35. An apparatus as claimed in claim 30, further comprising means, coupled to said converting means and responsive to said calculating means, for determining a zero level for said converting means and wherein said calculating means is also for autozeroing.

36. An apparatus as claimed in claim 30, further comprising means, coupled to said converting means and responsive to said calculating means, for determining a calibration of said converting means.

37. An apparatus as claimed in claim 30, further comprising: first switch means, interposed between said source of RF radiation and said cell, and responsive to said calculating means, for controlling connection between said source of RF radiation and said cell in response to a signal from said calculating means.

38. An apparatus as claimed in claim 37, further comprising second switch means, interposed between said source of RF radiation and said calibration source, and responsive to said calculating means, for controlling connection between source of RF radiation and said calibration source in response to a signal from said calculating means.

39. An apparatus as claimed in claim 30, further comprising means, responsive to said calculating means, for providing a visual indication of said change in concentration.

40. A method of analyzing a sample, comprising the steps of:
   (a) generating a first signal of radio frequency electromagnetic radiation;
   (b) direction said first signal along a path passing through a volume element of a sample;
   (c) measuring the rate of change of attenuation of said first signal as said first signal propagates along said path, and
   (d) determining a concentration of a chemical constituent in said volume element on the basis of the rate of change in said attenuation measured in said step (c).

41. A method of analyzing a sample as claimed in claim 40, further comprising the additional steps after said step (d) of:
   (e) providing a visual display indicative of the concentration calculated in said step (d).

42. A method of analyzing a sample, comprising the steps of:
   (a) generating a first signal of amplitude stabilized radio frequency electromagnetic radiation;
   (b) propagating said first signal radiation along a known path through a sample;
   (c) inducing a change of concentration of at least one chemical component of said sample for which a change in concentration induces a change in attenuation of the first signal;
   (d) measuring as said change of concentration occurs an amplitude of said first signal after it has traversed said known path;
   (e) repeating said step (d) to determine a rate of change of attenuation of said first signal; and
   (f) determining a change in concentration of said component on the basis of said rate of change of attenuation.

43. A method of analyzing a sample as claimed in claim 41, further comprising a first step of initiating a chemical reaction in said volume element of said sample, and wherein in steps (c) and (d) thereof, an initial rate of change of attenuation is measured and an initial concentration is determined, respectively.

* * * * *